(12) United States Patent
Suehira et al.

(10) Patent No.: US 8,634,081 B2
(45) Date of Patent: Jan. 21, 2014

(54) TOMOGRAPHIC IMAGING METHOD AND TOMOGRAPHIC IMAGING APPARATUS

(75) Inventors: Nobuhito Suehira, Kawasaki (JP); Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 266 days.

(21) Appl. No.: 13/287,380

(22) Filed: Nov. 2, 2011

(65) Prior Publication Data
US 2012/0133950 A1 May 31, 2012

(30) Foreign Application Priority Data

Nov. 26, 2010 (JP) ................................. 2010-263694

(51) Int. Cl.
*G01B 9/02* (2006.01)

(52) U.S. Cl.
USPC .......................................................... 356/479

(58) Field of Classification Search
USPC ................. 356/479, 497; 250/227.19, 227.27
See application file for complete search history.

(56) References Cited

U.S. PATENT DOCUMENTS

| | | | |
|---|---|---|---|
| 7,695,140 B2 | 4/2010 | Fercher | |
| 7,828,437 B2 * | 11/2010 | Kikawa et al. | 351/206 |
| 2008/0284981 A1 | 11/2008 | Fercher | |
| 2010/0182612 A1 * | 7/2010 | Yoshida et al. | 356/511 |
| 2010/0226553 A1 | 9/2010 | Suehira | |
| 2010/0226554 A1 | 9/2010 | Suehira | |
| 2011/0058175 A1 | 3/2011 | Suehira | |
| 2011/0096333 A1 | 4/2011 | Suehira et al. | |
| 2011/0098560 A1 | 4/2011 | Suehira et al. | |
| 2011/0134392 A1 | 6/2011 | Iwase et al. | |
| 2011/0137157 A1 | 6/2011 | Imamura et al. | |
| 2011/0267583 A1 * | 11/2011 | Hayashi | 351/206 |
| 2011/0299035 A1 | 12/2011 | Suehira | |
| 2012/0044499 A1 | 2/2012 | Shimoyama et al. | |

FOREIGN PATENT DOCUMENTS

JP          2009165518 A     *   7/2009

* cited by examiner

*Primary Examiner* — Michael A Lyons
(74) *Attorney, Agent, or Firm* — Fitzpatrick, Cella, Harper & Scinto (57) ABSTRACT

Provided is a tomographic imaging method, which acquires tomographic images of an object to be inspected, based on combined beams respectively acquired by combining reference beams and return beams acquired by irradiating the object to be inspected with a plurality of measuring beams. The tomographic imaging method includes a first step of acquiring the respective combined beams by reflecting information regarding the plurality of measuring beams which is stored in advance and irradiating the object to be inspected with the plurality of measuring beams, and a second step of generating the tomographic images based on the respective combined beams.

17 Claims, 5 Drawing Sheets

TOMOGRAPHIC IMAGING METHOD AND TOMOGRAPHIC IMAGING APPARATUS

BACKGROUND OF THE INVENTION

1. Field of the Invention

The present invention relates to a tomographic imaging apparatus and a tomographic imaging method, and more particularly, to a tomographic imaging method and a tomographic imaging apparatus which are used for ophthalmologic diagnosis and treatment.

2. Description of the Related Art

Currently, there are used various types of ophthalmologic apparatus using an optical instrument. Examples of the optical instrument for observing an eye include an anterior ocular segment photographing device, a fundus camera, and a confocal scanning laser ophthalmoscope (SLO). Of those, an optical tomographic imaging apparatus employing optical coherence tomography (OCT) which utilizes a low coherence beam is an apparatus capable of acquiring with a high resolution a tomographic image of an object to be inspected, and is thus becoming an indispensable apparatus as the ophthalmologic apparatus in outpatient treatment specialized in retina. Hereinbelow, this apparatus is referred to as OCT apparatus.

The OCT apparatus can measure cross-sections of an object to be inspected by splitting a low coherence beam into a reference beam and a measuring beam, irradiating the object to be inspected with the measuring beam, and causing interference to occur between a return beam from the object to be inspected and the reference beam. In other words, by scanning the object to be inspected with the measuring beam, a two-dimensional or three-dimensional tomographic image can be acquired. However, in a case where the object to be inspected is a living body such as an eye, movement of the eye causes a problem of image distortion. Thus, it is required that a high-sensitivity measurement be executed with high speed.

As one method for achieving this, U.S. Patent Publication No. 2008/0284981 discloses a method of simultaneously measuring a plurality of points of an object to be inspected. According to this method, by splitting a beam from a single light source, a plurality of beams is generated. Then, those beams are split by a beamsplitter into a plurality of measuring beams and reference beams, respectively. The object to be inspected is irradiated with the measuring beams, and return beams from the object to be inspected and the reference beams are combined by the beamsplitter. Then, the plurality of combined beams is caused to enter a grating, and resultant beams are simultaneously detected by a two-dimensional sensor. In this manner, U.S. Patent Publication No. 2008/0284981 attempts to achieve high speed by executing a simultaneous measurement using the plurality of measuring beams.

In the case where a plurality of points is simultaneously measured, depending on the apparatus configuration, the initial condition of the optical system needs to be measured in advance. Specifically, the apparatus has various tolerances, and hence, in some cases, a plurality of points cannot be measured under a desired condition. For example, there occurs a case where the measured area of each beam is displaced on a plane perpendicular to the optical axis, or there occurs a case where the measured area of each beam is displaced with respect to the optical axis direction (depth). If a measurement is executed without any consideration of such cases, a desired area cannot be measured.

SUMMARY OF THE INVENTION

In order to solve the above-mentioned problem, the present invention has been made, and therefore has an object of enabling a desired measurement to be executed by measuring an initial condition of an optical system and reflecting measurement results to a measurement of an object to be inspected.

In order to solve the above-mentioned problem, a tomographic imaging method used for an object to be inspected according to the present invention is an imaging method which acquires a plurality of tomographic images of an object to be inspected, based on a plurality of combined beams, respectively, which are acquired by combining a plurality of return beams and a plurality of reference beams, the plurality of return beams being acquired by irradiating the object to be inspected with a plurality of measuring beams, the plurality of reference beams respectively corresponding to the plurality of measuring beams, the imaging method including: correcting an apparatus condition so that a displacement value of each of the plurality of tomographic images is suppressed to a predetermined value or lower; and acquiring the plurality of tomographic images under the corrected apparatus condition.

Further, in order to solve the above-mentioned problem, a tomographic imaging apparatus according to the present invention is an imaging apparatus which acquires a plurality of tomographic images of an object to be inspected, based on a plurality of combined beams, respectively, which are acquired by combining a plurality of return beams and a plurality of reference beams, the plurality of return beams being acquired by irradiating the object to be inspected with a plurality of measuring beams, the plurality of reference beams respectively corresponding to the plurality of measuring beams, the imaging apparatus including: a correction unit for correcting an apparatus condition so that a displacement value of each of the plurality of tomographic images is suppressed to a predetermined value or lower; and an acquisition unit for acquiring the plurality of tomographic images under the corrected apparatus condition.

According to the present invention, a desired image can be acquired by measuring the initial condition of the optical system in advance and reflecting the measurement results to the measurement of the object to be inspected.

Further features of the present invention will become apparent from the following description of exemplary embodiments with reference to the attached drawings.

DESCRIPTION OF THE EMBODIMENTS

In a tomographic imaging apparatus according to an embodiment mode of the present invention, an object to be inspected is irradiated with a plurality of measuring beams via measurement light paths, and return beams thereof are respectively guided to detection positions via the measurement light paths. A scanner enables each of the measuring beams to scan the object to be inspected. Further, reference beams are guided to the detection positions via reference light paths for the reference beams. Then, the return beams and the reference beams guided to the detection positions are detected by a sensor as combined beams acquired by combining those beams. On the reference light paths, there is disposed a mirror, and the position of the mirror can be adjusted by operating a stage.

Further, a tomographic imaging method according to the embodiment mode of the present invention includes a first step of acquiring, based on information regarding a plurality of measuring beams which is stored in advance, respective combined beams by adjusting an irradiation condition of each of the measuring beams and irradiating an object to be inspected with those beams, and a second step of generating tomographic images based on the respective combined beams. Further, the tomographic imaging method may further include a third step of correcting each tomographic image thus generated based on the above-mentioned information.

First Embodiment

Hereinbelow, a first embodiment of the present invention is described in detail with reference to the drawings. This embodiment is particularly effective in a case where movement of an object to be inspected can be ignored.

Figure 2:
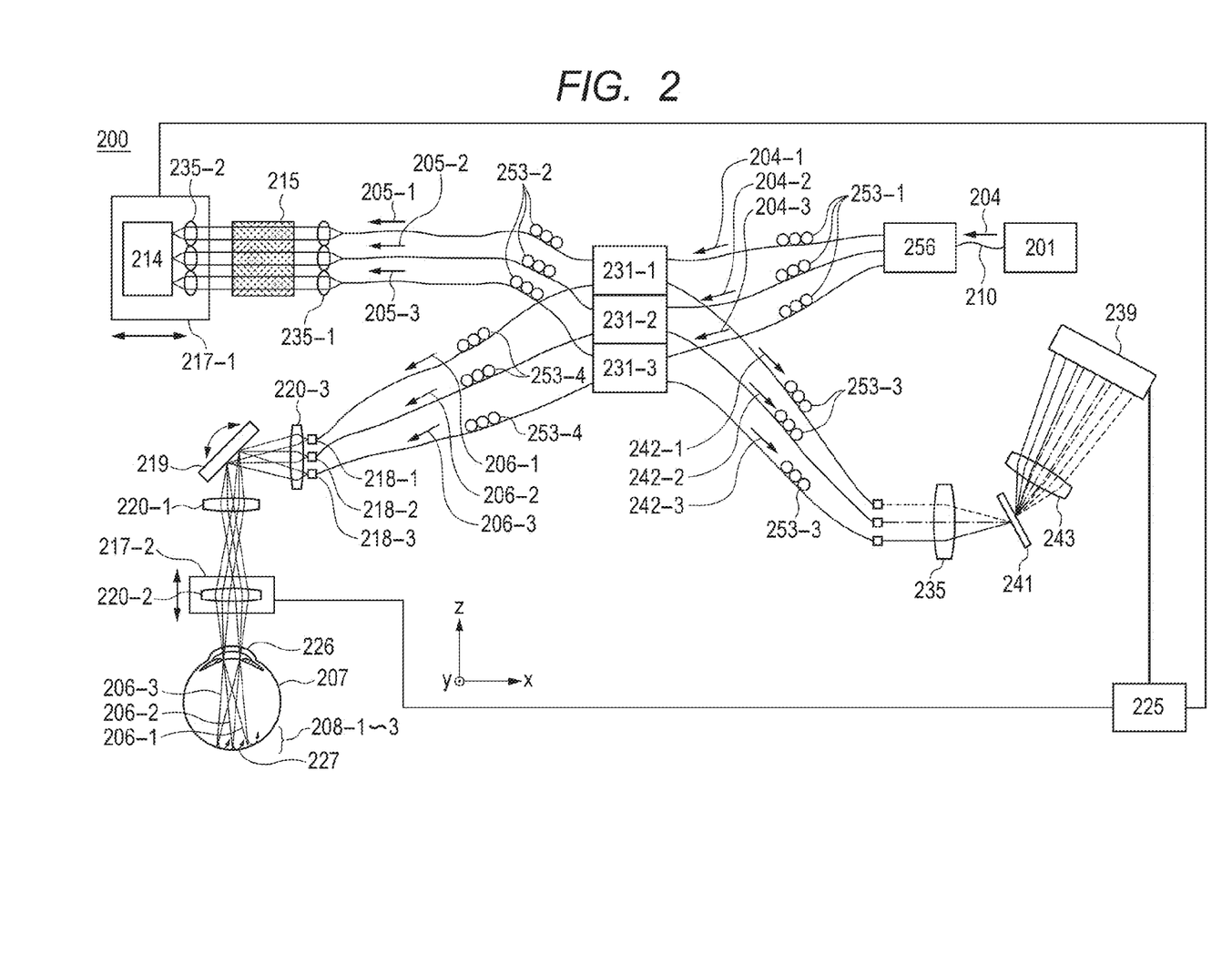
FIG. 2 is a diagram illustrating an apparatus configuration according to the first embodiment of the present invention.

FIG. 2 is a diagram illustrating a configuration of a tomographic imaging apparatus using light according to this embodiment. As illustrated in FIG. 2, an optical coherence tomography (OCT) apparatus 200 forms a Michelson interferometer as a whole.

(Optical System)

An outgoing beam 204 emitted from a light source 201 is guided by a single mode fiber 210 to enter an optical coupler 256, and is then split at the optical coupler 256 into outgoing beams 204-1 to 204-3, which pass through three optical paths of a first optical path, a second optical path, and a third optical path, respectively. Further, the three outgoing beams 204-1 to 204-3 pass through polarization controllers 253-1, and are then split at optical couplers 231-1 to 231-3 into reference beams 205-1 to 205-3 and measuring beams 206-1 to 206-3, respectively. The three measuring beams 206-1 to 206-3 thus acquired are returned as return beams 208-1 to 208-3, respectively, after being reflected or scattered at respective measurement regions in, for example, a retina 227 of an eye 207 to be inspected, which is an observation target. Then, the return beams 208-1 to 208-3 are respectively combined with the reference beams 205-1 to 205-3 coming through reference light paths by the optical couplers 231-1 to 231-3, with the result that combined beams 242-1 to 242-3 are acquired. The combined beams 242-1 to 242-3 are divided according to the wavelength by a transmission grating 241, and the divided beams enter different areas of a line sensor 239. The line sensor 239 converts, at each sensor element, the light intensity of each wavelength to voltage. By using a resultant signal, a tomographic image of the eye 207 to be inspected is acquired.

Next, matters related to the light source 201 are described. The light source 201 is formed of a super luminescent diode (SLD) that is a typical low coherence light source. Considering that the measuring beam is used for measuring an eye, the wavelength of the measuring beam preferably falls within the near-infrared light region. Further, the wavelength affects the resolution of the acquired tomographic image in the lateral direction, and hence the wavelength is desirably as short as possible. In this embodiment, the central wavelength is 840 nm and the bandwidth is 50 nm. Depending on the measurement region to be observed, another wavelength may be selected. The light source of SLD type is used in this embodiment, but an amplified spontaneous emission (ASE) type or the like may be used as long as the light source emits a low coherence beam. It is to be understood that the number of light sources may correspond to the number of measuring beams.

Next, the reference light paths of the reference beams 205 are described. The three reference beams 205-1 to 205-3 split by the optical couplers 231-1 to 231-3 pass through polarization controllers 253-2. A lens 235-1 substantially collimates the reference beams 205-1 to 205-3, and then emits resultant beams. Next, the reference beams 205-1 to 205-3 pass through dispersion compensation glass 215, and are respectively focused by lenses 235-2 onto a mirror 214. Then, the reference beams 205-1 to 205-3 change their directions at the mirror 214, and travel toward the optical couplers 231-1 to 231-3 again. The reference beams 205-1 to 205-3 pass through the optical couplers 231-1 to 231-3, respectively, and are then guided to the line sensor 239. Note that, the dispersion compensation glass 215 is for compensating for, with respect to the reference beams 205, the dispersion that occurs when the measuring beams 206 travel through the scanning optical system to and from the eye 207 to be inspected. Note that, as the average diameter of an eyeball of Japanese people, a typical value is assumed, which is 23 mm.

Further, an electric stage 217-1 is capable of moving in directions indicated by arrows in FIG. 2, and hence the optical path length of the reference beams 205 can be adjusted and controlled. The electric stage 217-1 is controlled by a computer 225. By the way, a position in a measurement light path, which has the same optical distance as a position in the reference light path, is called a coherence gate. By controlling the electric stage, the coherence gate can be adjusted, and thus the measurement range in a depth direction can be set. Note that, in this embodiment, the mirror 214, the electric stage 217-1, and the dispersion compensation glass 215 are shared among the three optical paths, but may be separately provided for each optical path.

Next, the measurement light paths of the measuring beams 206 are described. The measuring beams 206-1 to 206-3, which have been split by the optical couplers 231-1 to 231-3, respectively, pass through polarization controllers 253-4, and are then emitted from fiber end faces 218-1 to 218-3. Then, the resultant beams are substantially collimated by a lens 220-3, and are made to enter a mirror of an XY scanner 219 constituting the scanning optical system. In this embodiment, for the sake of simplicity, the XY scanner 219 is described as a single mirror. However, in actuality, the XY scanner 219 has two mirrors, that is, a mirror for X scan and a mirror for Y scan, disposed in proximity of each other, and executes raster scan over the retina 227 in a direction perpendicular to the optical axis. Further, a lens 220-1, the lens 220-3, and the like are adjusted so that the center of each of the measuring beams 206-1 to 206-3 coincides substantially with the rotation center of the mirror of the XY scanner 219. The lens 220-1 and a lens 220-2 constitute an optical system for causing the measuring beams 206-1 to 206-3 to scan the retina 227. In the optical system, the measuring beams 206 are caused to scan the retina 227 with vicinities of a cornea 226 being pivotal points. The measuring beams 206-1 to 206-3 each form an image at an arbitrary position on the retina.

Further, an electric stage 217-2 is capable of moving in directions indicated by arrows in FIG. 2, and hence the position of the lens 220-2 attached thereto can be adjusted and controlled. By adjusting the position of the lens 220-2, each of the measuring beams 206-1 to 206-3 can be focused for observation onto a desired layer of the retina 227 of the eye 207 to be inspected. The measuring beams 206-1 to 206-3 enter the eye 207 to be inspected, and after being reflected and scattered by the retina 227, become the return beams 208-1 to 208-3. The return beams 208-1 to 208-3 pass through the optical couplers 231-1 to 231-3, respectively, and are then guided to the line sensor 239. Note that, the electric stage 217-2 is controlled by the computer 225. With the above-mentioned configuration, the three measuring beams are scanned simultaneously.

Next, a configuration of a detection system is described. The return beams 208-1 to 208-3 reflected and scattered at the retina 227 are combined with the reference beams 205-1 to 205-3 by the optical couplers 231-1 to 231-3, respectively. Then, the combined beams 242-1 to 242-3 thus acquired enter a spectroscope, with the result that spectra are acquired. The computer 225 executes signal processing on those spectra.

(Spectroscope)

The spectroscope is now described in detail. In this configuration, a plurality of combined beams is processed with a single line sensor, and hence cost reduction can be achieved compared to a two-dimensional sensor.

Figure 3:
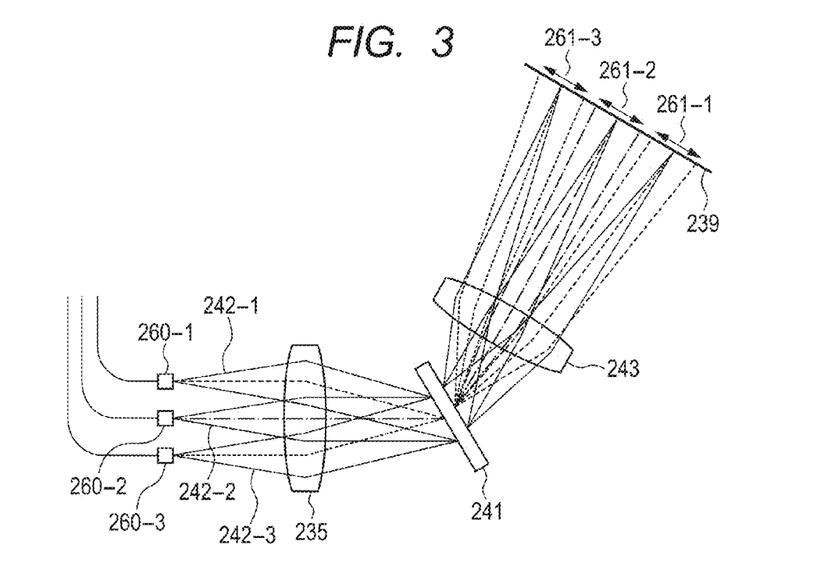
FIG. 3 is a diagram illustrating a spectroscope according to the first embodiment of the present invention.

For the purpose of describing in detail the spectroscope portion illustrated in FIG. 2, FIG. 3 illustrates a configuration in the case where the three combined beams (242-1 to 242-3) enter the spectroscope. Fiber end faces 260-1 to 260-3 are disposed so as to be separated from one another, and the combined beams 242-1 to 242-3 are emitted from the fiber end faces 260-1 to 260-3, respectively. On this occasion, the directions of the fiber end faces 260-1 to 260-3 are adjusted in advance so that the combined beams 242-1 to 242-3 perpendicularly enter a principal plane of a lens 235, that is, so that telecentricity is achieved. Each of the three combined beams 242-1 to 242-3 is substantially collimated by the lens 235, and all the three combined beams 242-1 to 242-3 enter the transmission grating 241.

In order to reduce loss of light amount, it is necessary that the transmission grating 241 be positioned in the vicinity of a pupil of the optical system, and that the transmission grating 241 be provided with an aperture on a surface thereof. Further, the transmission grating 241 is disposed in an inclined manner with respect to the principal plane of the lens 235, and hence the beams form an oval figure on the surface of the transmission grating 241. Accordingly, the aperture provided on the surface of the transmission grating 241 needs to be oval. The combined beams 242-1 to 242-3 diffracted by the transmission grating 241 enter a lens 243. Here, in FIG. 2, as for the diffracted combined beams, only beams having the central wavelength are illustrated, and as for the diffracted combined beams having the other wavelengths, only principal rays are illustrated for the sake of simplicity. The combined beams 242-1 to 242-3, which have entered the lens 243 after being diffracted, respectively form images on the line sensor 239, and spectra are observed at positions indicated by arrows 261-1 to 261-3.

TABLE 1

Relation between combined beam and imaging position on line sensor according to first embodiment

| Combined beam | Incident angle (°) | Wavelength λ | Diffraction angle (°) | Imaging position (mm) | Number of pixels |
|---|---|---|---|---|---|
| 242-1 | 37.11 | 815.00 | 22.00 | −21.78 | 833 |
|  |  | 840.00 | 23.87 | −16.81 |  |
|  |  | 865.00 | 25.77 | −11.80 |  |
| 242-2 | 30.26 | 815.00 | 28.29 | −5.16 | 870 |
|  |  | 840.00 | 30.26 | 0.00 |  |
|  |  | 865.00 | 32.28 | 5.27 |  |
| 242-3 | 23.42 | 815.00 | 35.49 | 13.71 | 964 |
|  |  | 840.00 | 37.63 | 19.38 |  |
|  |  | 865.00 | 39.83 | 25.27 |  |

Table 1 shows the upper limit and the lower limit of the wavelength and the central wavelength (840 nm) of the measuring beam to be used in this embodiment. It can be understood that the combined beams 242-1 to 242-3 have different diffraction angles due to differences in incident angles with respect to the transmission grating, resulting in different imaging positions among the combined beams. Further, the number of pixels to be used when detection is executed with the sensor element having a pixel size of 12 μm varies depending on the combined beam.

(Correction of Apparatus)

Next, an example of acquiring and correcting basic information on the apparatus is described. By executing a correction, even when a plurality of measuring beams is used, data acquired therefrom can be handled in the same manner as data acquired from a single measuring beam. In other cases, according to the shape of an object to be inspected, for example, curvature, the position of the coherence gate can be shifted by a necessary amount before measurement. Such issues do not occur in the case of a tomography apparatus using a single measuring beam.

The necessity for the correction is now described in further detail. In some cases, the optical path system has a mechanical tolerance and thus is not always identical to the design value. In other cases, due to various limitations, the optical path system is designed in consideration of the correction from the beginning. For example, in some cases, the fiber end faces 218-1 to 218-3 have tolerances in their positioning, and the positions of imaging areas (XY plane) of the measuring beams in the fundus may differ from the designed positions. Further, due to the fact that the measuring beams pass through different optical paths, the imaging areas may have different sizes. When the fiber end face is adjusted, the adjustment needs to be executed with precision on the order of micrometers. For those reasons, the range of the XY plane is corrected at the time of measurement, and hence it is possible to measure a desired area. Here, a configuration of the present invention for suppressing, to a predetermined level or lower, the displacement amount of each tomographic image acquired from each of the plurality of measuring beams is collectively referred to as means for correcting an apparatus condition according to the present invention. In this case, it is preferred that the means for correcting the apparatus condition correct the imaging range of each of the plurality of imaging areas (XY plane) based on information regarding each of the plurality of measuring beams. However, in a case where the fiber end face can be adjusted as described above, the position of the fiber end face, which is the emission position of the measuring beam, may be adjusted. Note that, in this embodiment, the position adjustment in the XY plane cannot be executed among the fibers, and hence a further correction is required after images are acquired.

Next, another example is described. In the Z direction, the position of the coherence gate may differ from the design value due to, for example, tolerances of the length of the fiber, tolerances of optical components such as the lens and the dispersion compensation glass, and tolerances of mechanical parts such as the mirror and the scanner. The coherence gate refers to such a position in the measurement light path that has the same optical distance as a position in the reference light path. The coherence gate can be moved by moving the position of the mirror 214. By executing a correction at the time of measurement, a desired measurement can be executed. Specifically, by controlling each of the optical path lengths of the reference beams, an operation is executed to equalize the imaging ranges of the corresponding measuring beams in the depth direction of the object to be inspected. This operation is executed with the configuration included as the means for correcting the apparatus condition according to the present invention. Note that, in this embodiment, the characteristics of the spectroscope differ depending on the measuring beam, and hence the measurable depth, the attenuation characteristics due to roll-off, the depth resolution, and the like differ. Those need to be corrected after images are acquired.

In this example, an eye model is used for the correction. The eye model is a glass ball having the same optical characteristics, size, and volume as a living eye. In the fundus portion of the eye model of this example, there are arranged cocentric circles and a radial pattern. Signals acquired by scanning the three measuring beams 206-1 to 206-3 with the XY scanner 219 are detected by the line sensor 239, and the data thus detected is acquired by the computer 225.

Figure 4A:
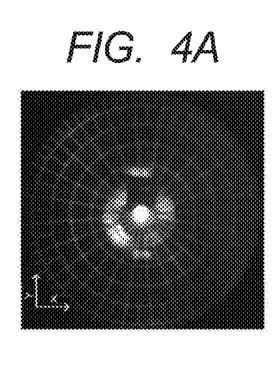
FIG. 4A is a fundus image of an eye model according to the first embodiment of the present invention.
Figure 4B:
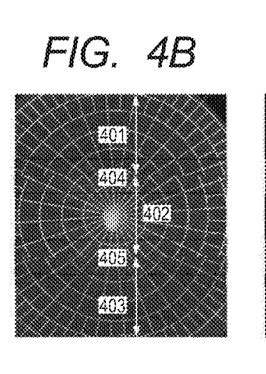
FIG. 4B is a two-dimensional intensity image according to the first embodiment of the present invention.
Figure 4C:
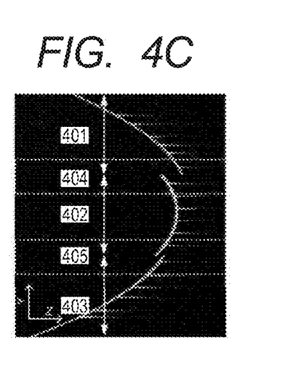
FIG. 4C is a tomographic image stretching across areas according to the first embodiment of the present invention.

FIGS. 4A, 4B, and 4C show an example of measuring the eye model by the plurality of measuring beams. The eye model is fixed at a position at which the eye to be inspected is actually disposed, and a measurement is executed. FIG. 4A is a fundus image acquired by a fundus observing mechanism (not shown), FIG. 4B is a two-dimensional intensity image, and FIG. 4C is a tomographic image of the first line stretching across three measurement areas. Corresponding to the three measuring beams, there are a first area 401 scanned with the measuring beam 206-1, a second area 402 scanned with the measuring beam 206-2, and a third area 403 scanned with the measuring beam 206-3, which are indicated by solid white arrows. Then, at the boundaries of those areas, there exist a first overlapping area 404 and a second overlapping area 405, which are sectioned by dotted lines. Those overlapping areas are treated as boundary areas of individual tomographic images. The eye model does not move during the measurement, and hence those overlapping portions have a match, and by removing those portions, the two-dimensional intensity images and the tomographic images can be connected without any incongruity. Note that, in this embodiment, each tomographic image is disposed so as to have an overlapping area, but each tomographic image may be disposed so as not to have such an overlapping area. In this case, in order to connect the two-dimensional intensity images and the tomographic images without any incongruity, interpolation data may be generated as data constituting a connection portion of each image, thereby connecting the respective images based on that data. Alternatively, by using the interpolation data, images located on both sides of that data may be shifted with that data set as the center, to thereby connect the images.

With the analysis of the measurement data of the eye model, it can be seen that there is a difference of several tens of micrometers from the design value in each of the X direction and the Y direction in the XY plane among the measuring beams, but the magnification is substantially the same as designed. Specifically, by adding such a range that corresponds to the difference when the scanner executes the scan, it is possible to measure a desired range. This configuration of executing the scan corresponds to the means for correcting the apparatus condition according to the present invention, and in this case, it is preferred that the range corresponding to the difference be added by adjusting the scan angle of the scanner. Regarding the Z direction, it can be seen that the position of the coherence gate is displaced by several hundreds of micrometers from the design value.

This difference is serious for OCT. Specifically, assuming that the depth resolution is 6 μm and that the number of pixels of the spectroscope is 1,000, the measurable depth is 6 μm×500=3 mm. A difference of several hundreds of micrometers raises a fear that a desired area cannot be measured. If the position of the coherence gate is adjusted so as to eliminate this difference, the data can be handled in the same manner as in the measurement using a single measuring beam. Specifically, by controlling each of the optical path lengths of the reference beams, an operation is executed so as to differentiate at least one of the imaging ranges of the corresponding measuring beams in the depth direction of the object to be inspected from the other imaging ranges. This operation is executed by the configuration included as the means for correcting the apparatus condition according to the present invention. Specifically, in this case, it is preferred that the means for correcting the apparatus condition adjust the coherence gate based on information regarding each of the measuring beams. Note that, the correction of the depth resolution is adjusted so that when the coherence gate is shifted by the same amount, the same number of pixels are shifted in the tomographic image. The adjustment of the depth resolution in the tomographic image is executed by, for example, zero padding in which zeros are added to the data of the spectroscope.

The position of the coherence gate is adjusted by using the overlapping area. As another method, the scan may be executed in such a scan direction that the image of FIG. 4C can be acquired with a single measurement so that the tomographic images are connected without any incongruity. Information (correction value) necessary for correcting a difference or the like, which is acquired from the measurement data, is stored for each apparatus in a storage portion of the computer 225. Note that, the necessary information described above contains at least one of the irradiation position of each measuring beam on a plane perpendicular to the measuring beam, the imaging magnification, a displacement of each measuring beam in the optical axis direction, and the resolution of the tomographic image.

By reflecting those pieces of information to the apparatus as initial information, and executing a correction at the end, a desired measurement can be executed. Specifically, based on the initial information, a measurement is executed by correcting the apparatus condition regarding at least one of the position of the coherence gate and the position of the imaging area, and a correction is further executed so as to ensure continuity of the thus acquired data. Further, the correction of the apparatus condition is executed for the purpose of suppressing the displacement amount or value of the individual image to the predetermined level (value) or lower with regard to each of the plurality of tomographic images and the two-dimensional intensity images corresponding to each of the plurality of measuring beams described above. In this embodiment, the apparatus condition refers to the condition of each component of the apparatus for changing at least one of the position of the coherence gate and the imaging area.

However, the apparatus condition is preferably construed as including all the conditions of the components capable of changing the above-mentioned displacement amount. For example, in a case where the apparatus condition is adjusted so as to acquire substantially the same results as in the measurement executed by using a single measuring beam, the outlines of the eye model of FIGS. 4B and 4C become continuous. Conversely, by utilizing the characteristics of the three measuring beams, the coherence gates can be separately shifted to execute a measurement. Specifically, in FIG. 4C, when the curvature of the eye model is large, in some cases, a measurement cannot be executed in the entire area. In such a case, by arranging the coherence gates so that the positions of the eye model in the areas 401 and 403 are shifted rightward in FIG. 4C, it becomes possible to execute a measurement in a wider area. Note that, FIG. 4C represents initial value data before the correction, and thus the outlines of the eye model in the areas 401 and 403 are asymmetrical and shifted toward the right-hand side from the beginning. In this example, this means that intentional control is executed. Then, by executing a correction based on the correction value at the end, continuous images can be acquired. As described above, the above-mentioned predetermined level refers to such a displacement amount that, when a plurality of images of areas to be inspected within the scanning ranges of the measuring beams is displayed on a single screen, enables the respective images to be connected, and enables the areas to be inspected to be displayed as a single image.

Specifically, in this embodiment, when the plurality of tomographic images is acquired based on the combined beams acquired from the plurality of measuring beams and reference beams, there exists an overlapping area in each tomographic image. For example, by using the eye model described above, a plurality of first tomographic images is generated, and in areas where the first tomographic images overlap each other, each displacement amount is examined. This displacement poses a problem when tomographic images of an eye to be inspected or an object to be inspected are actually generated. Hence, the above-mentioned apparatus conditions such as the position of the coherence gate and the resolution are adjusted so that, when the individual tomographic images are displayed on the same screen, the displacement amount is suppressed to the predetermined level or lower at which the displacement amount of each overlapping area is correctable with the signal processing to be executed later. Note that, the tomographic images to be used at the time of the adjustment may be images stored in advance or may be images taken and stored immediately before the adjustment. After the adjustment or the correction of the apparatus condition or the displacement amount is finished, a plurality of second tomographic images is generated based on the irradiation of the measuring beams with respect to the object to be inspected and on the combined beam. In the plurality of second tomographic images acquired at this stage, the displacement amount of each of the second tomographic images in the overlapping area is in a state in which each displacement can be recognized in a single screen as illustrated in, for example, FIG. 4C. The signal processing and the like to be described later are carried out on the plurality of second tomographic images, and a correction is executed so as to ensure continuity for each of the second tomographic images in the overlapping area. With the above-mentioned steps, one continuous tomographic image can be acquired.

(Signal Processing)

Figure 1:
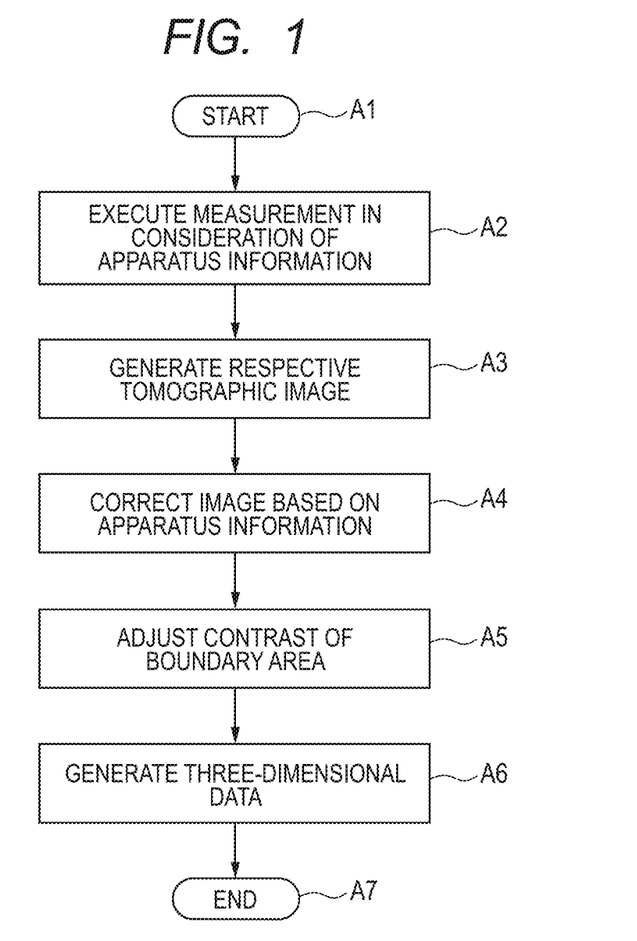
FIG. 1 is a diagram illustrating an embodiment mode of the present invention.

FIG. 1 illustrates a signal processing step according to the first embodiment. Note that, each step is implemented through operation of each component under control of the computer 225.

In a step A1, a measurement is started. In this state, the OCT apparatus is in operation, and the eye to be inspected is disposed. Further, adjustment necessary for the measurement has already been executed by an operator.

In a step A2, already-acquired apparatus information is reflected to thereby execute the measurement. First, the coherence gates are disposed so as to acquire a desired measurement condition. In this example, in the desired measurement condition, the measurement executed by using the three measuring beams is handled in the same manner as the measurement executed by using a single measuring beam. Specifically, the coherence gates are disposed so that the positions of Z=0 of FIG. 4C become identical.

After the measurement, a signal of a plurality of combined beams is acquired. For example, the scan is executed for 512 lines in the X direction and for 200 lines in the Y direction. The combined beams 242-1 to 242-3 acquired from the three measuring beams enter the line sensor 239, and as a result, A-scan data (4,096 pixels) having a one-dimensional array is acquired. Then, data corresponding to the sequential 512 lines in the X direction is stored with B-scan data having a two-dimensional array as a unit (4,096×512 pixels, 12 bits). By the time the scan is finished, 200 pieces of this data are stored for one measurement.

In a step A3, respective tomographic images are generated. First, fixed noise is removed. Next, in consideration of a fact that the A-scan data of each measuring beam has equal intervals with respect to the wavelength, wavelength-wavenumber conversion is executed thereon, thereby acquiring the A-scan data having equal intervals with respect to the wavenumber. Then, a discrete Fourier transform is carried out on this data, thereby acquiring intensity data with respect to the depth.

In a step A4, each of the acquired tomographic images is corrected based on the initial information (correction value) of the apparatus, for example, on information stored regarding each of the measuring beams. In the spectroscope, the areas where respective detection beams form an image on the line sensor differ from one another, and accordingly, a numerical resolution in the depth direction per pixel and the attenuation characteristics (roll-off) in the depth direction vary. Based on the apparatus information, resampling is executed in the Z direction to thereby equalize the resolution in the depth direction. In this example, the resolution of the second measuring beam (measuring beam whose measurement area is at the central portion) is set as a reference distance per pixel. Further, a correction for equalizing the attenuation characteristics in the depth direction is executed. Further, based on the stored correction value, the XY position and the Z position of each of the tomographic images are determined, and the magnification is corrected. With this, the imaging range of each of the tomographic images is adjusted or controlled.

In a step A5, the contrast of each of the tomographic images is adjusted. The adjustment is executed so that the dynamic range of the image, which differs due to differences in noise and transmittance, is equalized in each of the measurement areas. Specifically, the entire images of the respective measurement areas are adjusted so that the tomographic images of the B-scan at the same position, which have been measured by different measuring beams in the boundary areas 404 and 405, have the same contrast.

In a step A6, three-dimensional data is generated. A result acquired in the step A5 is stored as data having a three-dimensional array.

Note that, in the case where the coherence gates of the plurality of measuring beams are separately controlled, the coherence gates are controlled to be at desired positions in the step A2, and a correction is executed in the step A4.

Even in the case where a measurement is executed with a plurality of measuring beams as described above, it is possible to execute a desired measurement by using the initial information of the apparatus.

Second Embodiment

This embodiment is particularly effective in a case where a measurement is executed on an object to be inspected which moves during the measurement. In the tomographic image of each measurement area, B-scan images adjacent to each other within each measurement area are substantially continuous. On the other hand, B-scan images in the boundary area may be significantly shifted from each other. If a two-dimensional intensity image or a slow scan image is created in such a situation, in some cases, it is difficult to acquire a continuously connected image even after a correction is executed on the apparatus. Here, a difference from the first embodiment is particularly described.

(Signal Processing)

Figure 5:
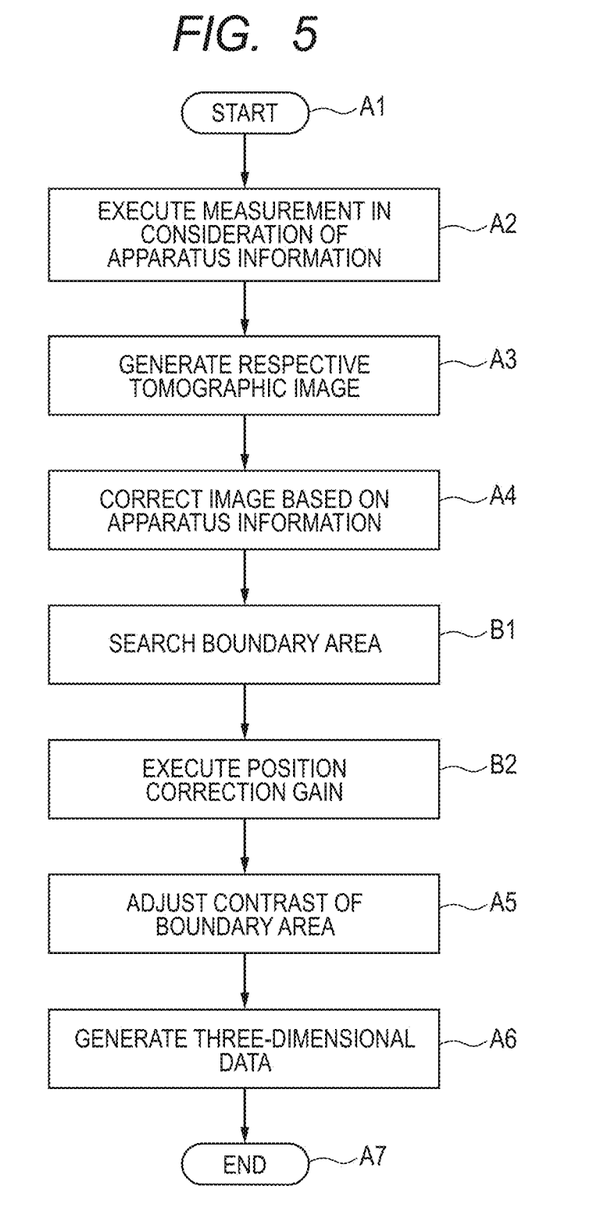
FIG. 5 is a diagram illustrating a signal processing step according to a second embodiment of the present invention.

FIG. 5 illustrates a signal processing step according to a second embodiment of the present invention.

In the step A1, a measurement is started.

In the step A2, the measurement is started based on the apparatus information. It is to be understood that the measurement area may be determined in consideration of the characteristics of the object to be inspected, in addition to the apparatus information. In this example, the measurement is executed over, for example, a range of mm in the X direction with 500 lines. The scan is executed for, for example, 192 lines in the Y direction, and there is an overlapping area of 20% for each measuring beam. The setting is such that the measurement is executed over 10 mm with 500 lines with the overlapping areas excluded. In a case where 500 lines are acquired with a line rate of 50 kHz, a measurement time per image is 12 msec if a return time of the scanner is considered. Assuming that the object to be inspected is a human eye and that the model moves 0.1 mm per second at maximum in the X and Y directions during the measurement, the model moves 230 µm at maximum in consideration of 192×12 msec. The measurement area is determined in view of such movements.

In the step A3, respective tomographic images are generated.

In the step A4, a correction is executed based on the initial information (correction value) of the apparatus.

Figure 6A:
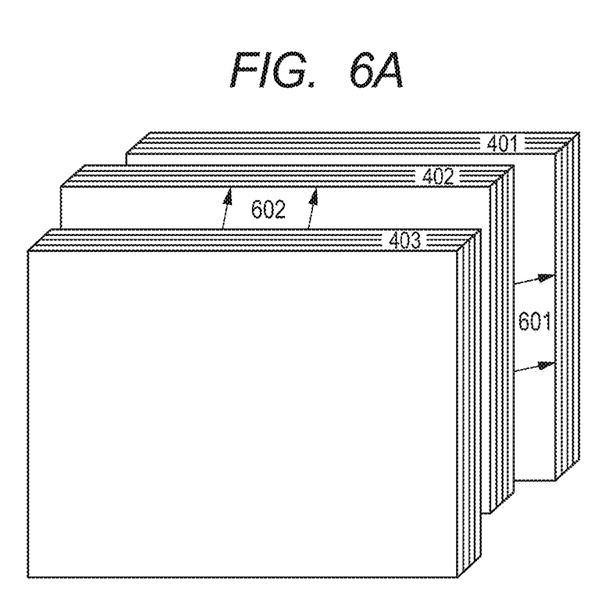
FIG. 6A is a diagram illustrating three-dimensional arrangement of tomographic images according to the second embodiment of the present invention.

In a step B1, the boundary area is searched. This is described with reference to FIGS. 6A and 6B. FIG. 6A illustrates three-dimensional arrangement of tomographic images acquired by the respective measuring beams. The tomographic images in the first area 401, the second area 402, and the third area 403 are respectively numbered from 0 to 191. Then, the 154th to 191st images in the first area 401 are designed to correspond in order to the 0th to 37th images in the second area 402. Similarly, the 154th to 191st images in the second area 402 are designed to correspond to the 0th to 37th images in the third area 403. In this example, when there is an overlapping area, the tomographic images in the second area are used. It is to be understood that the first and third areas may be used, or a comparison may be made to select a tomographic image having a better contrast. Note that, the overlapping area corresponds to the boundary area to be described later.

In the search, an image closest to the 0th image in the second area is searched for in order from the 154th image in the first area and extracted. The range may be determined based on a measurement time of one image and general movement of the object to be inspected. It is assumed that the object to be inspected is a human eye and that the model moves 230 µm per second at maximum during the measurement. In the case where the range of 10 mm is divided by 500, the resolution is 20 µm, and hence the search only needs to be made for about 12 images with the 154th image set at the center. In the same manner, an image closest to the 191st image in the second area is searched for in order from the 37th image in the third area and extracted. It is to be understood that if the model is appropriate, the overlapping area of 20% (38 images) is too wide, and 12 images suffice.

The method for the search may be a general method. For example, some feature points of each tomographic image are extracted, and images having the smallest differences among those feature points are determined as having a match. Alternatively, in another example, tomographic images having the highest similarity therebetween are determined as the tomographic images having a match. As a function for evaluating the similarity, a normalized cross-correlation function may be used. Note that, in some cases, the search cannot be executed for reasons such as the object to be inspected having moved significantly, and there being no image due to a blink. In such cases, images are connected based on the design value.

Here, the description is given by assuming that, with regard to the Y direction, the 154th image in the first area and the 0th image in the second area have a match, and the 191st image in the second area and the 37th image in the third area have a match as designed. Further, based on each set of the images having a match, the positional displacement of the first area with respect to the second area and the positional displacement of the third area with respect to the second area are calculated. Note that, in FIG. 6A, a relationship between the 154th image in the first area and the 0th image in the second area is expressed by a vector as a first displacement amount 601. In the same manner, a relationship between the 191st image in the second area and the 37th image in the third area is expressed by a vector as a second displacement amount 602.

In a step B2, the position adjustment is executed again. In other words, a displacement between the tomographic images is corrected. The vectors acquired in the above-mentioned step are provided as the initial values to the first area and the third area, and the positions of the respective tomographic images are arranged in three-dimensional coordinates. Specifically, the positional relationship of FIG. 6A is acquired. Then, the 0th to 153rd images in the first area, the 0th to 191st images in the second area, and the 38th to 191st images in the third area, that is, 500 images in total, are arranged in a continuous manner.

In the step A5, the contrast of the boundary area is adjusted. Specifically, the contrasts of the first and third areas are adjusted so that the contrast of the 154th image in the first area coincides with the contrast of the 0th image in the second area, and that the contrast of the 191st image in the second area coincides with the 37th image in the third area. Then, such adjustment is applied to the tomographic image in the first area and the tomographic image in the third area.

Figure 6B:
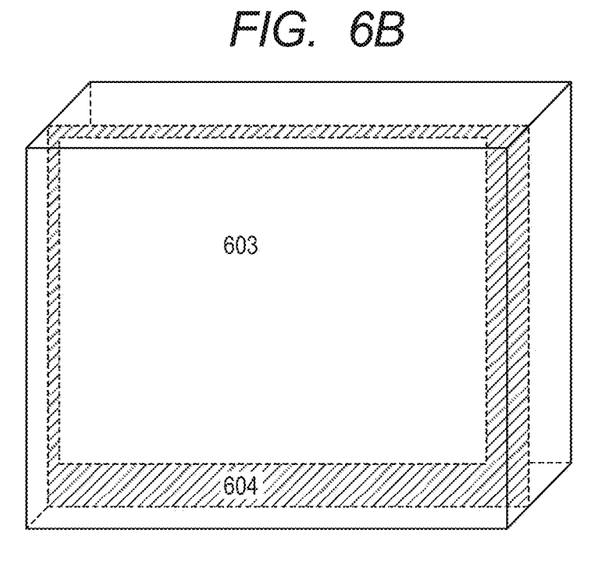
FIG. 6B is a diagram illustrating tomographic image data after rearrangement according to the second embodiment of the present invention.

In the step A6, three-dimensional data is generated. A result acquired in the step A5 is stored as three-dimensional data. FIG. 6B schematically illustrates the tomographic image. A measurement area 603 represents the 37th image in the third area. Due to the positional displacement, additional data 604 is added to acquire new data. The additional data has a noise level of zero or a noise level corresponding to the background of the measurement area 603. Consequently, the data is added to FIG. 6A, with the result that three-dimensional data having such a cubic shape as illustrated in FIG. 6B is acquired. When the tomographic image is displayed, even if arbitrary cross-sections are displayed continuously, the structure of the object to be inspected can be displayed continuously without any incongruity. Note that, instead of adding the additional data, the three-dimensional data may be created by deleting data of discontinuous portions.

In the case where the object to be inspected moves, the effect of the movement of the object to be inspected can be reduced by adding a function of tracking the movement of an eye, for example. Further, with the provision of a function of detecting a blink, by executing processing of taking an image again in the case of a blink, it is possible to prevent the omission of data. Further, by comparing the fundus image and the two-dimensional intensity image, it is possible to improve positioning accuracy for the images.

As described above, even in the case where different measuring beams are used and the object to be inspected may move during the measurement, desired three-dimensional data can be acquired.

OTHER EMBODIMENTS

Further, the present invention is also implemented by executing the following processing. Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-263694, filed Nov. 26, 2010, which is hereby incorporated by reference herein in its entirety.

What is claimed is:

1. An imaging method, which acquires a plurality of tomographic images of an object to be inspected, based on a plurality of combined beams, respectively, which are acquired by combining a plurality of return beams and a plurality of reference beams,
   the plurality of return beams being acquired by irradiating the object to be inspected with a plurality of measuring beams,
   the plurality of reference beams respectively corresponding to the plurality of measuring beams,
   the imaging method comprising:
   correcting an apparatus condition so that a displacement value of each of the plurality of tomographic images is suppressed to a predetermined value or lower; and
   acquiring the plurality of tomographic images under the corrected apparatus condition.

2. An imaging method according to claim 1, wherein the correcting of the apparatus condition comprises correcting the apparatus condition based on information regarding the plurality of measuring beams which is stored in advance.

3. An imaging method according to claim 2, wherein the plurality of combined beams are acquired by scanning the object to be inspected with the plurality of measuring beams based on the information.

4. An imaging method according to claim 2, wherein the information comprises at least one of a position of each of the plurality of measuring beams on a plane perpendicular to the plurality of measuring beams, a magnification, a displacement of each of the plurality of measuring beams in an axial direction, and a resolution.

5. An imaging method according to claim 2, wherein the information is acquired by using an eye model.

6. An imaging method according to claim 2, further comprising:
   searching a boundary area, which is an area where two of the plurality of tomographic images overlap each other, after correcting the plurality of tomographic images; and
   correcting a displacement of the two of the plurality of tomographic images in the boundary area.

7. An imaging method according to claim 1, further comprising correcting the plurality of tomographic images based on information regarding the plurality of measuring beams which is stored in advance.

8. An imaging method, which acquires a plurality of tomographic images of an object to be inspected, based on a plurality of combined beams, respectively, which are acquired by combining a plurality of return beams and a plurality of reference beams,
   the plurality of return beams being acquired by irradiating the object to be inspected with a plurality of measuring beams,
   the plurality of reference beams respectively corresponding to the plurality of measuring beams,
   the imaging method comprising:
   generating and storing a plurality of first tomographic images by using the plurality of measuring beams, which are used for generating the plurality of first tomographic images having an overlapping area therebetween and respectively correspond to the plurality of first tomographic images;
   correcting an apparatus condition based on the stored plurality of first tomographic images so that each displacement value between two of the plurality of first tomographic images in the overlapping area is suppressed to a predetermined value or lower;
   acquiring, after the correcting of the apparatus condition, a plurality of combined beams respectively corresponding to the plurality of measuring beams by irradiating the object to be inspected with the plurality of measuring beams;
   generating, based on the plurality of combined beams, respectively, a plurality of second tomographic images having an overlapping area therebetween and respectively corresponding to the plurality of combined beams; and
   executing a correction so as to ensure continuity for each of the plurality of second tomographic images in the overlapping area where two of the plurality of second tomographic images overlap each other.

9. An imaging method according to claim 8, wherein the correcting of the apparatus condition is executed by changing at least one of a position of a coherence gate and a position of an imaging area, which correspond to each of the plurality of measuring beams.

10. An imaging apparatus, which acquires a plurality of tomographic images of an object to be inspected, based on a plurality of combined beams, respectively, which are acquired by combining a plurality of return beams and a plurality of reference beams, the plurality of return beams being acquired by irradiating the object to be inspected with a plurality of measuring beams, the plurality of reference beams respectively corresponding to the plurality of measuring beams, the imaging apparatus comprising:

a correction unit for correcting an apparatus condition so that a displacement value of each of the plurality of tomographic images is suppressed to a predetermined value or lower; and an acquisition unit for acquiring the plurality of tomographic images under the corrected apparatus condition.

11. An imaging apparatus according to claim 10, wherein the correction unit corrects the apparatus condition based on information regarding the plurality of measuring beams which is stored in advance.

12. An imaging apparatus according to claim 11, wherein the correction unit corrects, based on the information, the apparatus condition by changing at least one of a position of a coherence gate and a position of an imaging area, which correspond to each of the plurality of measuring beams.

13. An imaging apparatus according to claim 11, wherein the correction unit corrects, based on the information, the apparatus condition by changing an emission position of each of the plurality of measuring beams.

14. An imaging apparatus according to claim 11, wherein the correction unit corrects, based on the information, the apparatus condition by changing a scan angle of each of the plurality of measuring beams on the object to be inspected.

15. An imaging apparatus according to claim 10, further comprising a tomographic image correcting unit for correcting the plurality of tomographic images based on information regarding the plurality of measuring beams which is stored in advance.

16. An imaging apparatus according to claim 10, wherein the correction unit comprises a control unit for controlling an optical path length of each of the plurality of reference beams, and wherein the control unit controls respective imaging ranges of the plurality of measuring beams in a depth direction of the object to be inspected so that the respective imaging ranges become equal to each other.

17. An imaging apparatus according to claim 10, wherein the correction unit comprises a control unit for controlling an optical path length of each of the plurality of reference beams, and wherein the control unit controls respective imaging ranges of the plurality of measuring beams in a depth direction of the object to be inspected so that at least one of the respective imaging ranges becomes different from other imaging ranges.

* * * * *